United States Patent [19]

Melchior et al.

[11] Patent Number: 4,835,605
[45] Date of Patent: May 30, 1989

[54] METHOD FOR THE DETERMINATION OF A GEOMETRICAL PARAMETER FOR CRIMPED, IRREGULARLY STRUCTURED FIBRES

[75] Inventors: Klaus Melchior, Besigheim; Manfred Rueff, Geradstetten; Hartmut Federle, Ahrensburg, all of Fed. Rep. of Germany

[73] Assignees: FHG, Munich; B.A.T. Cigarettenfabriken GmbH, Hamburg, both of Fed. Rep. of Germany

[21] Appl. No.: 40,777

[22] PCT Filed: Aug. 8, 1986

[86] PCT No.: PCT/DE86/00322
§ 371 Date: Jun. 26, 1987
§ 102(e) Date: Jun. 26, 1987

[87] PCT Pub. No.: WO87/01195
PCT Pub. Date: Feb. 26, 1987

[30] Foreign Application Priority Data

Aug. 14, 1985 [DE] Fed. Rep. of Germany ....... 3529137
Jul. 30, 1986 [DE] Fed. Rep. of Germany ....... 3625791

[51] Int. Cl.[4] .............................................. H04N 7/18
[52] U.S. Cl. .................................. 358/107; 358/101; 382/18
[58] Field of Search .................. 358/106, 101, 107; 382/8.1, 18; 356/383, 384, 387; 364/474, 478, 562

[56] References Cited

U.S. PATENT DOCUMENTS

| | | | |
|---|---|---|---|
| 3,968,475 | 7/1976 | McMahon | 382/18 X |
| 4,460,921 | 7/1984 | Henry et al. | 358/107 |
| 4,547,800 | 10/1985 | Masaki | 358/107 |
| 4,636,849 | 1/1987 | Wada et al. | 358/106 |

Primary Examiner—James J. Groody
Assistant Examiner—Victor R. Kostak
Attorney, Agent, or Firm—Ralf H. Siegemund

[57] ABSTRACT

The invention relates to a method for determining a parameter for fibres, particularly for crimped, irregularly structured fibres, such as textile fibres and tobacco fibres. A given quantity of fibres is separated on a substrate. Two congruent images of the separated fibres is produced with a camera. By means of a grid, the number of grid elements covered by the fibres is determined from the superimposed congruent images. The images are then mutually displaced by one and/or more grid steps $(\Delta x_o, \Delta y_o)$ in $(-x)$ and $(+y)$ and $(x/\pm y)$ (diagonally). (For symmetry reasons the $(-x)$ and $(-y)$ displacements give the same results as the $(+x)$, $(+y)$ displacements and the $(-x/\pm y)$ displacements give the same results as the $(+x/\pm y)$ displacements. The number of grid elements with fibres of the two images still covering one another following the displacement is determined and added to the number of grid elements with fibres of the non-displaced images. By dividing the result by the number of grid elements with fibres of the non-displaced images, the geometrical parameter is obtained. Division is a standardization procedure. Thus, the parameter is independent of the fibre quantity applied.

2 Claims, 4 Drawing Sheets

METHOD FOR THE DETERMINATION OF A GEOMETRICAL PARAMETER FOR CRIMPED, IRREGULARLY STRUCTURED FIBRES

TECHNICAL FIELD

The invention relates to a method for determining a geometrical parameter for a mixture of crimped, curly or crinkled, irregularly structured fibres of different length and width, such as textile fibres and tobacco fibres with the features of the preamble of claim 1.

PRIOR ART

The average fibre length is a geometrical quantity for straight fibres having a uniform thickness, but a different length. This can be determined in such a way that a quantity of fibres is separated or singled out on a defined surface of a substrate, an image of the separated fibres is produced by means of a camera, the length of the individual fibres is measured from the image, the lengths of the individual fibres are summated and the sum is divided by the number of fibres. The thus obtained geometrical parameter is the average fibre length (cf. e.g. "Messen+Prüfen, Automatik", October 1983, pp 546 to 556). All these methods are carried out with one image per measurement.

In the case of crimped fibres with a uniform fibre diameter, such as textile fibres and crimped fibres with different fibre width and branches of the individual fibres, such as e.g. tobacco fibres, the average fibre length is not a suitable geometrical parameter for characterizing a fibre mixture, because an average fibre length cannot be determined and because branches, different fibre widths along a single fibre and fibre crimping are not taken into consideration.

DESCRIPTION OF THE INVENTION

The problem of the present invention is therefore to provide a method according to the preamble of claim 1 making it possible to determine a geometrical parameter for crimped, irregularly structured fibres in a fibre mixture with a large number of fibres, which is able to characterize fibres with an irregular fibre structure in crimping, length, width and diameter.

According to the invention this problem is solved by the method stages given in the characterizing part of claim 1. Further developments of the invention are described in subclaim 2.

The advantages of the invention are in particular that by producing two images and subsequent raster or grid formation and the displacement of said grids or rasters with respect to one another, it is possible to form a parameter for characterizing a fibre mixture making it possible to evaluate and classify said fibre mixture according to its characteristics, which are of decisive importance e.g. for the quality control of the fibre mixture.

SHORT DESCRIPTION OF THE DRAWINGS

The invention is described in greater detail hereinafter relative to the drawings, wherein show:

FIG. 1, A picture of a separated quantity of fibres.

FIG. 2, A picture of a separated quantity of fibres with a superimposed transparent identical image, which is displace by one grid step (approximately 1 mm) (+x) direction.

FIG. 2a, A larger scale, diagrammatic representation of the displacement in the (x) or (+y) or (x/±y) direction by in each case grid step $x_o$, $y_o$—description of the coordinate system, details of the grid steps $\Delta x_o$, $\Delta y_o$.

FIG. 2b, A master or reference image in the starting position—hatched surface: surface F to be determined.

FIG. 2c, A master or reference image and displaced image; displacement by $\Delta x_o$ in the +x direction—hatched surface: surface to be determined on displacement by one unit ($\Delta x_o$) in the +x direction.

FIG. 2d, The master image and displaced image; displacement by $\Delta y_o$ in the +y direction—hatched surface: surface to be determined on displacing by one unit ($\Delta y_o$) in the +y direction.

FIG. 2e, Master image and displaced image; displacement by $\Delta y_o$ in the +y direction and by $\Delta x_o$ in the +x direction—hatched surface: surface to be determined.

FIG. 2f, Master image and displaced image; displacement by $\Delta y_o$ in the −y direction and by $\Delta x_o$ in the +x direction—hatched surface: surface to be determined.

FIG. 4 is a flow chart showing how the invention is to be performed.

BEST WAY OF PERFORMING THE INVENTION

Figure 1:
Figure 1:
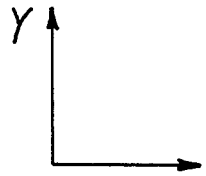

FIG. 1 is a picture, e.g. a slide of a quantity of fibres (tobacco fibres), which are arranged in separate or singled out form on a clearly defined surface of 5×5 cm, so that no individual fibre overlapping occurs. The individual fibres are crimped and have different fibre lengths and different fibre thicknesses along an individual fibre, which in the case of tobacco fibres can come from leaf veins and branches. By means of a fine grid or raster placed beneath them, the grid elements are counted by means of a counter, covered by the individual fibres and summated. The sum gives the surface F covered by the individual covers, measured in grid units.

Figure 2:
Figure 2:
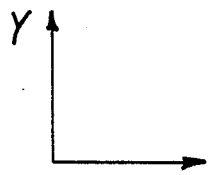

FIG. 2 is the slide according to FIG. 1 with drawn through lines. On said slide is placed an identical slide (a necessary prerequisite for the measuring method described here), which is displaced by one raster step in the (+x) direction and is indicated in hatched form. According to method step (c) of claim 1 for each individual fibre the grid elements are determined by means of a counter, which is covered by both slides. In a similar manner the grid elements are determined both for slides displaced in the (+y) direction and also diagonally in the (x/y) direction by in each case one grid unit.

The grid elements which overlap in all these displacements are summated and added to surface F giving a new surface F′>F. For standardization purposes surface F′ is divided by F determined with the image not displaced. Surfaces F and F′ are measured in grid units, which gives the geometrical parameter for characterizing crimped, irregularly structured fibres according to the invention. For the even more precise determination of the parameter, it is possible for the displacement to take place by several grid steps in the (+x) or (−y) or (x/±y) direction and in each case the still overlapping grid elements are determined by means of a counter and added to surface F.

Tests have shown that an adequately accurate parameter can be obtained with two displacements in the particular directions. The greater the number of grid steps, the larger the numerical value of the parameter.

Thus, parameters with different numbers of steps are not comparable.

It is advantageous to choose a square grid and one grid step corresponds at the maximum to the smallest fibre width of an individual fibre.

Figure 3A:
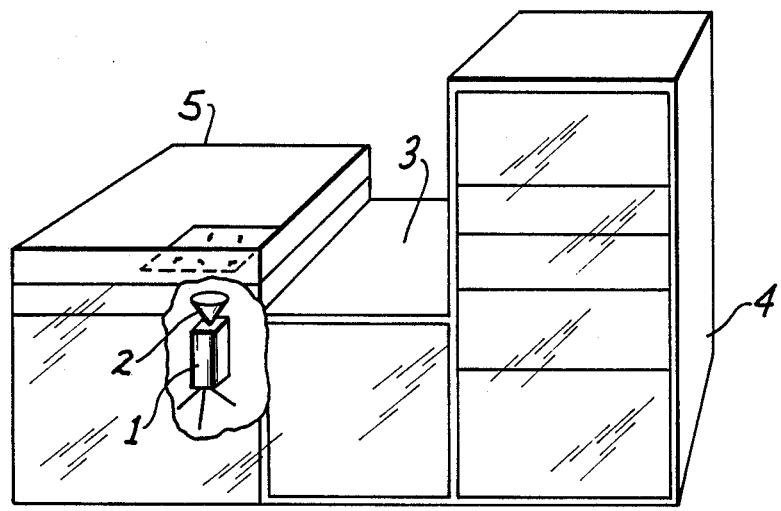
FIGS. 3a and 3b are respectively, a perspective view of the equipment for practicing the inventive method with FIG. 3b being a block diagram of that equipment.

According to a further development of the invention, as defined in claim 2, advantageously known image processing means are used for determining the parameter, which permit very fine grid steps. As shown in FIGS. 3a and 3b the equipment includes an electronic camera 1 which produces an optoelectronic grid image 2. The grid elements covered by the individual fibers 3 are digitally filed in the memory or digital store 6 of a digital computer 5 within a cabinet 4. The displacements of the grid images by (x), (+y), (x/±y), x/±2y), (2x), (2x/±y), (2x/±2y), (2y) are carried out in the digital computer, as are the determination of the overlapping raster elements and the calculation of the geometrical parameter according to method steps (b), (c) and (d) of claim 1 and for this purpose commercially available image processing means can be used. Reference numeral 5 refers to an illumination unit.

The mutual displacement of identical images and the determination of the still overlapping grid elements corresponds to an autocorrelation method.

INDUSTRIAL USABILITY

Figure 2A:
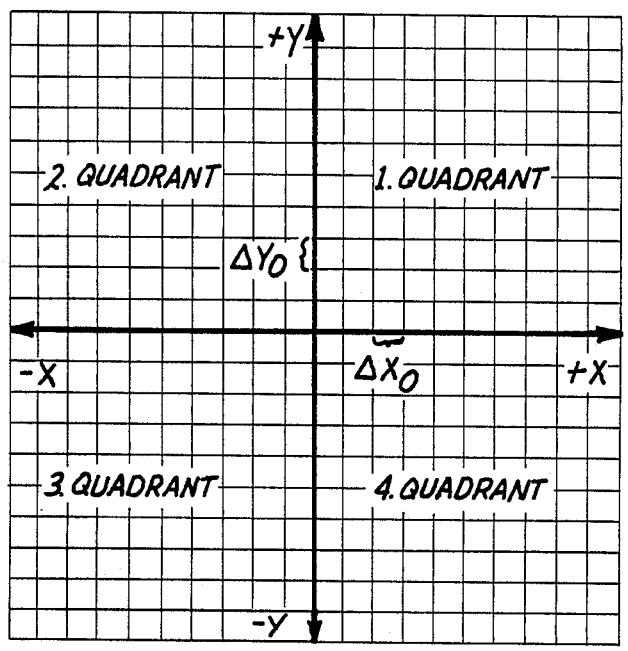
Figure 2B:
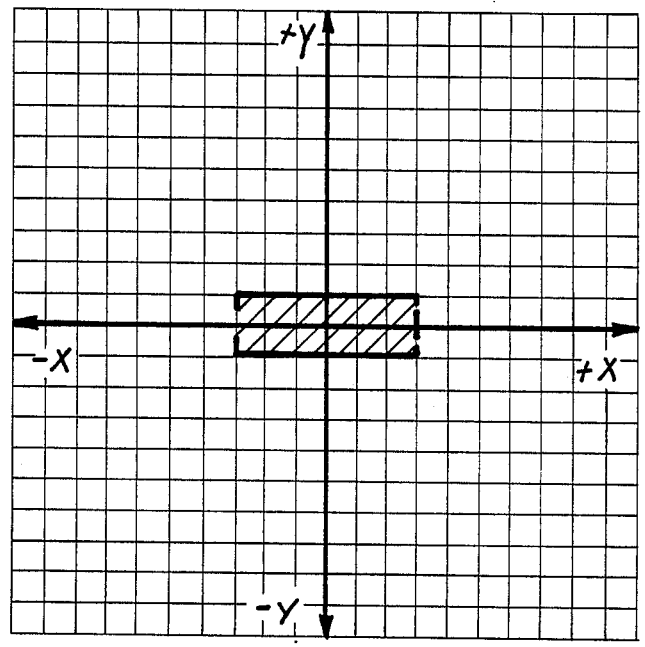
Figure 3:
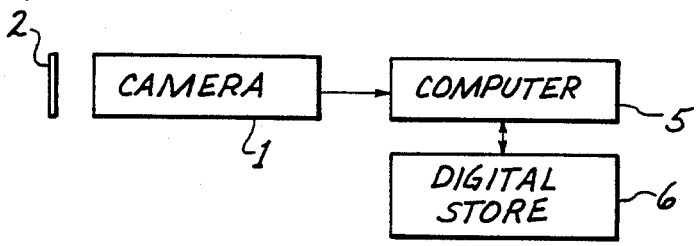
Figure 2C:
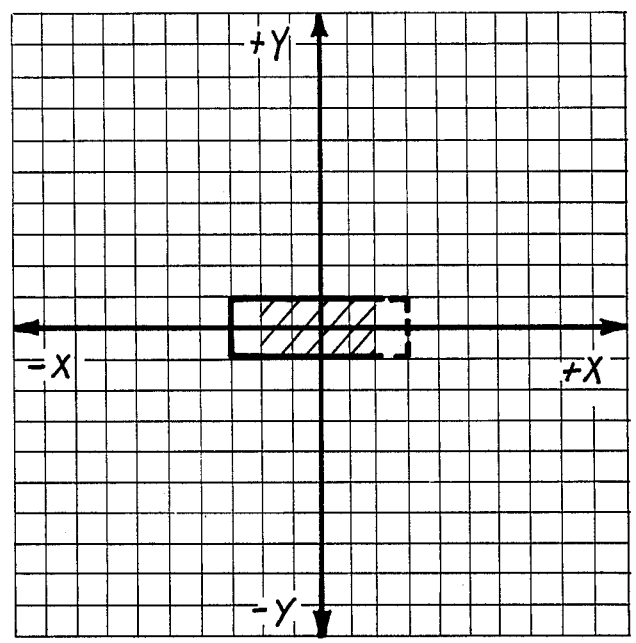
Figure 2D:
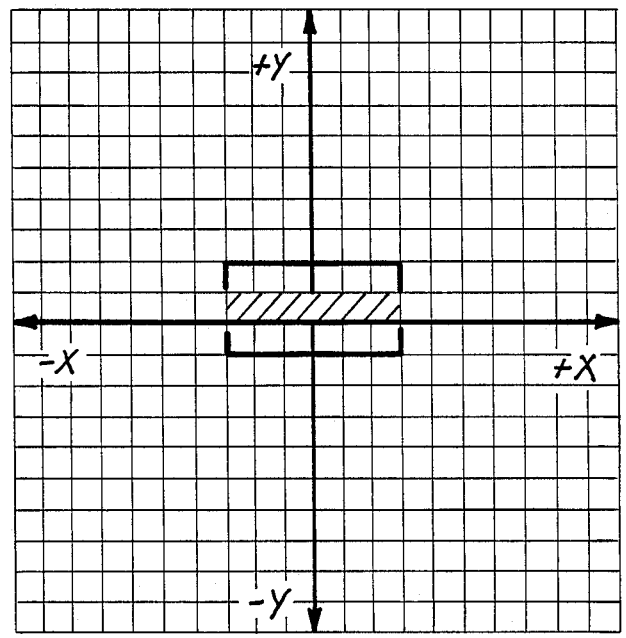
Figure 2E:
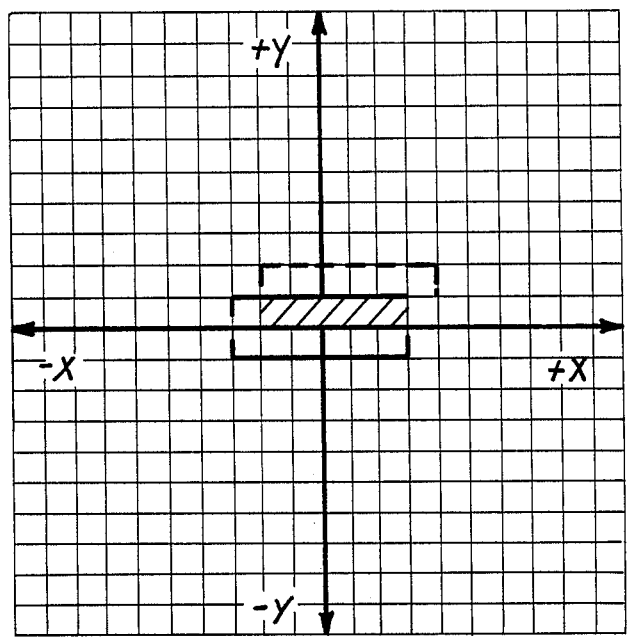
Figure 2F:
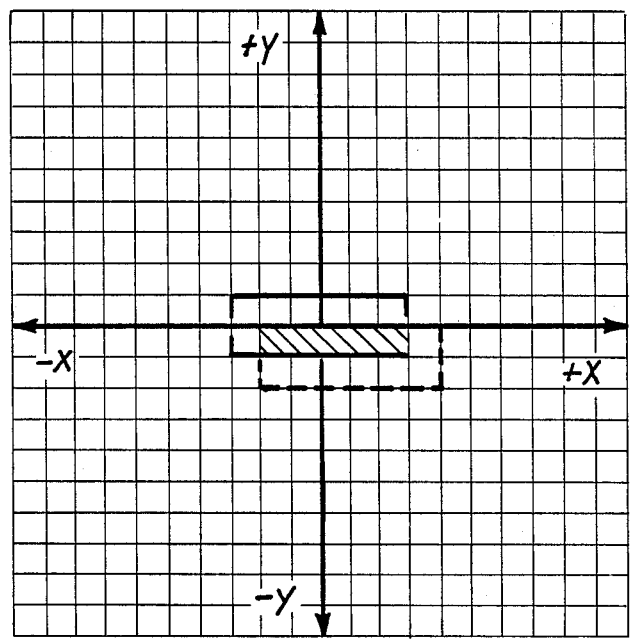

The following tests were carried out for determining the geometrical parameter for tobacco fibres. Cigarettes of different brands were opened. Part of the tobacco was removed from each individual cigarette and separated on a planar surface with the dimensions 5×5 cm. Method steps (b), (c) and (d) according to claim 1 were performed by means of an image processing system. For emphasizing the linear extension, firstly a weighting (first moment of the autocorrelation function) of the individual overlapping surfaces was carried out with the size of the step and secondly the displacements in the second and third quadrants were carried out (cf. FIG. 2a). Thus, the following parameters were obtained for two grid steps:

| Cigarette brand | Parameter |
|---|---|
| I | 18.3222 |
| II | 17.8687 |
| III | 16.0040 |
| IV | 16.2076 |
| V | 17.2862 |
| VI | 17.8863 |
| VII | 18.1727 |
| VIII | 18.4303 |
| IX | 18.8275 |
| X | 18.9407 |
| XI | 20.0150 |

The parameters of the individual cigarettes clearly differ. Supplementary tests can be carried out to establish how the parameter is influenced by different crimpings, different overlapping surfaces of individual fibres and different individual fibre widths (in the case of tobacco fibres veins and branches).

In the case of straight individual fibres with the same cross-section along said individual fibre, the parameter resulting from the method of the invention can be essentially allocated to the average fibre length.

What is claimed is:

1. Method for the determination of a geometrical parameter for a mixture of fibres of different length and width, including, separating a quantity of fibres on a clearly defined surface of a substrate, producing an image of the separated fibres by means of a camera; and determining measured values, geometrical parameters of the fibres from the image, the improvement comprising:
   (a) producing two congruent images,
   (b) determining grid elements by means of a grid said grid elements are covered by the fibres, the grid having been chosen in such a way that one grid step is at the most as wide as the thinnest point of an individual fibre,
   (c) the images mutually displacing by one or more grid steps in one direction (x);
   (d) determining the number of grid elements with fibres of the two images which are mutually overlapping after the displacement, by means of a counter,
   (e) displacing the images from the starting position in a direction at right angles thereto (+x) and subsequently diagonally in the (x/±y) direction by the same distance or distances;
   (f) determining subsequently the number of grid elements with fibres of the two images still overlapping after the displacements; and
   (g) adding the number of grid elements (surfaces) determined according to steps (b) through (f) and dividing the resulting sum by the number (F) of the grid elements determined according to step (b), so as to produce the desired parameter.

2. Method according to claim 1, characterized by using as an optical camera, an electronic camera, to produce an optoelectronic grid image; storing digitally the grid image in the memory of a digital computer, step stages (b) through (g) according to claim 1 are performed by the digital computer.

* * * * *